United States Patent [19]
Jin et al.

[11] Patent Number: 5,968,771
[45] Date of Patent: Oct. 19, 1999

[54] GLOBAL ISCHEMIA INDUCED GENE

[75] Inventors: Kun Lin Jin; Jun Chen; Steven H. Graham; Roger P. Simon, all of Pittsburgh, Pa.

[73] Assignee: University of Pittsburgh, Pittsburgh, Pa.

[21] Appl. No.: 08/891,837

[22] Filed: Jul. 14, 1997

[51] Int. Cl.$^6$ .............................. C12P 21/02; C12N 1/00; C12N 5/10; C12N 15/12
[52] U.S. Cl. ...................... 435/69.1; 435/243; 435/320.1; 435/325; 435/410; 536/23.5
[58] Field of Search ........................ 536/23.5; 435/320.1, 435/243, 325, 410, 69.1

[56] References Cited

PUBLICATIONS

Thompson, *Science* 267:1456 (1995).
Chen, J., et al., *J. Clin. Pathol.* 48: 7 (1995).
Linnik, M.D., et al., *Stroke* 24: 2002 (1993).
Chen, J., et al., *Neuroreport.* 6: 394 (1993).
Martinou, J.C., et al., *Neuron* 13: 1017 (1994).
Kane, et al., *Science* 262: 1274 (1993).
Hara, et al., *PNAS USA* 94: 2007 (1997).
Wilson, et al., *Curr. Biol.* 5: 32 (1995).
Englekamp, et.al., *Curr Opin Geret. Div.* 6: 334 (1996).
Williams, G.J., et.al., *Cell* 74: 777 (1993).
Clark, S.G., et.al., *Cell* 74: 43 (1993).
Nakamura, et.al., *Nat. Genet* 12: 154 (1996).
Andrews, et.al., *Science* 270: 251 (1995).
Doyle, et.al., *Nature* 323: 76 (1986).
Han et.al., *Cell* 56: 573 (1989).
Kohler, et.al., *Nature* 256: 495 (1975).
Pulsinelli, W.A., et.al., *Ann. Neural.* 11: 491 (1982).
Chomczynski, P., et.al., *Anal. Biochem* 162: 156 (1987).
Schalling, M., et.al., *Acta Physiol. Scand* 131: 631 (1987).
Wilcox, J.N., et.al., *J. Clin Invest.* 82: 1134 (1988).
Sanbrook, J., et.al., *Molecular Cloning, A Laboratory Manual* (2ed. 1989) Cold Spring Harbor Laboratory Press, pp. 18.60–18.75.
Harlow, E., et.al., *Antibodies: A Laboratory Manual*, Cold Spring Harbor Laboratory, p. 726 (1988).

*Primary Examiner*—Terry McKelvey
*Attorney, Agent, or Firm*—Reed Smith Shaw & McClay LLP

[57] ABSTRACT

The nucleotide sequence is provided for a novel death regulatory gene. In particular the present invention relates to a DNA segment encoding a giig15b gene; polypeptides encoded by that DNA segment; recombinant DNA molecules containing the DNA segment; cells containing the recombinant DNA molecule; a method of producing a giig15b peptide; and antibodies specific to giig15b protein.

9 Claims, 11 Drawing Sheets

| | |
|---|---|
| 1 | ATCAGCGCTCGCCCAGTCTTCATACGCTCACGGACC ATG TCG GCG CAG |
| |                                                                 Met Ser Ala Gln |
| 48 | ACT GGC AGC GGC CCC ACG GAG GAC CAG GTG GAG ATC CTG GAG TAC AAC |
| | Thr Gly Ser Gly Pro Thr Glu Asp Gln Val Glu Ile Leu Glu Tyr Asn |
| 97 | TTC AAC AAG GTC AAC AAG CAC CCC GAC CCC ACC ACG CTG TGC CTC ATC |
| | Phe Asn Lys Val Asn Lys His Pro Asp Pro Thr Thr Leu Cys Leu Ile |
| 145 | GCA GCC GAG GCG GGC CTC ACG GAG GAG CAG ACG CAG AAA TGG TTT AAG |
| | Ala Ala Glu Ala Gly Leu Thr Glu Glu Gln Thr Gln Lys Trp Phe Lys |
| 193 | CAG CGC CTG GCG GAG TGG CGG CGG TCA GAA GGC CTG CCT TCG GAA TGC |
| | Gln Arg Leu Ala Glu Trp Arg Arg Ser Glu Gly Leu Pro Ser Glu Cys |
| 241 | AGA TCG GTC ACG GAC TAGGGAGCCAGGCCCTTGAGCTTGCTCCCGGAACTTCCGTGCC |
| | Arg Ser Val Thr Asp |
| 299 | TCAGTTTACCCAGGCTGTTTTGATGTTTCAGTGCAGTGTTAATGTCTCATTGTTTGCTGCCT |
| 363 | GCTGTTTAACACAATGTGTTTTTTGAATGTATATAACTAAAGAAACAAAATAACAGGAAGCTA |
| 426 | AATGCAGTTCTGTGTAAAGCGATGGCTTGGCCGGGAGAGGGGTGTGGCTTACGTTTCTCTTTG |
| 489 | GATTTTAATGAAAGATGATGTGGGAGCAGTTTTTGTTTGCCCTTGACCGCCACTTTCCAATCC |
| 552 | GTATGTACCACCATCCGTTTCAGAGCATTCCAGAGCTGCCTGGCTTCTGTTGAGAAGTTAAAG |
| 615 | GAACGGGCAGGCAGGGGAGACACCTCAGTCCACCTTCCTGTGCCTCTTTCCTCGCTTCACTTA |
| 678 | ACACTCTGGTGGTTGGATGAGAACACGGGTGTATTTGAGTCATTCAATTTTTATATATTTGAA |
| 741 | ATATAGATATATAAAACAGTTCCTTCTCTTACAGCTGCGTTACCTTGGAAAACACCCTCGTTT |
| 804 | AGCAGCGACAGATTCCAAGGGGCAGAAAAGCAGGTAGCTAGGGAAAAAAAGTTACAGAGTCTA |
| 867 | GAATCTACCTTATTTAAATGAACTTGTTACATTTATTTTGCTGAATAACATGAACCGCTTTTT |
| 929 | TTTGTCTCAAAAATTATATTCTAAATAAAAAACTTTGAGAATCCAAAAAAAAAAAAAAA |

FIG. 2

```
1. GIG 15b    ED  VEI  VN NKV  H  PT LCL   RAG    QT K   Q       G  PSEC  VTD
2. M77842     QE  I A  KE ERTH-Y  VFARERL  KID   ARI   SN  F    E K RNQR QASN
3. S69508     QE  I A  KE ERTT-Y  VFARERL  KID   ARI   SN  F    E K RNQR QASN
4. L03394     DE  I A  NL QE-T Y  VG REQL  RKVH   KVEV  SN  P
5. M85271     DE  I A  NL QE-T Y  VG REQL  RKVH   KVEV  SN  P
6. D40856     DE  I A  NL QE-T Y  VG REQL  RRVH   KVEV  N   P
7. M81481     DE  I A  NL QE-T Y  VG REQL  RRVH   KVEV  N   P
8. L08401         I    KA SRTH-Y  VF REEL  MKIG   RI T  QN  F   KQ KVGPQSHP
9. U28145     QV  I    KE ERTH-Y  VFARERL  QKIQ   ARI   SN  F   RE KMRNK-
10. L37867    SH   TE  NW SR- RY  MACREE   UWIS   PRVRV  N      KR
```

FIG. 3

GLOBAL ISCHEMIA INDUCED GENE

FIELD OF THE INVENTION

The present invention relates generally to a gene that is expressed in the brain following neural injury. More particularly the present invention relates to cloning and sequencing a gene ("giig15b") that encodes a 7.1 kD protein ("giig15b") which contains a homeodomain. The expression of the gene is increased in neurons that are destined to die after ischemia and suppresses cell death in vitro. The present invention also relates to possible therapeutic uses of the DNA sequence, expressed polypeptides, and antibodies, for example, in developing diagnostic and therapeutic agents.

BACKGROUND OF THE INVENTION

Cell death in an organism is under genetic control. Genetically controlled cell death, also known as programmed cell death, has been best described during fetal development. As a normal part of development of an adult organism, cells that are not needed die via activation of a cascade of death-promoting genes. Meanwhile, other genes are expressed during development that promote survival of cells that are required in the adult. Besides elimination of unwanted cells during development, many adult cells turn over. For example, gastroepithelial cells die and are replaced by new cells constantly. This physiologic cell death also occurs via the process of programmed cell death. Many cells that undergo programmed cell death develop stereotypic morphologic changes referred to as apoptosis.

Yet other genes that control cell death have been discovered by cancer researchers. Cancer is a state where there are defects in genes that control normal programmed cell death. Mutations in a series of cancer causing genes (oncogenes) are necessary for the development of cancer. Thus, many genes that control programmed cell death are also oncogenes.

In the last several years it has become apparent that the genes that regulate programmed cell death are also important in cell death under pathologic conditions. Thompson, Science 267:1456 (1995). For example, in brain, expression of genes that regulate cell death is increased after such pathologic insults as ischemia and epilepsy. Chen, J., et al., J. Clin. Pathol. 48:7 (1995). Furthermore, DNA laddering, a biochemical hallmark of programmed cell death, and some of the morphologic changes that characterize apoptosis occur in these disease states. Linnik, M.D., et al., Stroke 24:2002 (1993). Alteration of expression of such death regulatory genes by various means alters outcome in cerebral ischemia. For example, the death regulatory gene bcl-2 is an oncogene which suppresses cell death. Its expression is induced after cerebral ischemia. Chen, J., et al., Neuroreport 6:394 (1993). Transgenic mice which express the human bcl-2 transgene have been shown to have smaller strokes after middle cerebral artery occlusion than wild-type mice. Martinou, J. C. et al., Neuron 13:1017 (1994). Furthermore, over expression of bcl-2 prevents programmed cell death of neurons in culture. Kane, et al., Science 262:1274 (1993).

Other genes that promote programmed cell death have also been implicated in ischemia and other neurologic diseases. For example, the cysteine proteases are a family of genes that promote programmed cell death during development. Cysteine protease inhibitors decrease the volume of infarction after middle cerebral occlusion in rats. Hara, et al., PNAS USA 94:2007 (1997). Thus, there is evidence that the expression and activity of these death regulatory genes may contribute to stroke and other neurologic diseases.

Transcription factors are proteins that bind to nuclear double stranded DNA and regulate the expression of other genes. Homeotic proteins (homeobox or HOX proteins) are a family of transcription factors that share a highly conserved amino acid sequence (the homeodomain) that is the site where the protein binds to DNA. The homeodomain is conserved from primitive organisms such as the nematode C. elegans to humans. The amino acid sequences that flank the highly conserved amino acid sequence are not conserved. These flanking regions determine which genes the respective homeobox proteins regulate. There have been over forty different human homeobox proteins identified. All of these proteins bind to a specific DNA sequence, the homeodomain-binding site. HOX genes regulate cell and organ differentiation during development. Wilson, et al., Curr. Biol. 5:32 (1995).

Programmed cell death requires a cascade of gene expression events. Early steps in this cascade include the expression of transcription factors. Englekamp, et al., Curr. Opin. Genet. Dev. 6:334 (1996). There are two examples of homeobox genes that regulate cell death as reported by Williams, G. J., et al., Cell 74:777 (1993). The apoptotic cell death of C. elegans somatic neurons is induced by the homeobox gene Lin-34. Clark, S. G., et al., Cell 74:43 (1993). Additionally, expression of some human homeobox genes is altered in neoplastic cells. Nakamura, et al., Nat. Genet. 12:154 (1996).

The mechanism by which neurons die in many disease states is not well understood. Furthermore, means of diagnosis of these conditions and methods of treatment are not available. Therefore, there remains a need for further elucidation of the genes that promote or suppress cell death, particularly in brain. Cloning and sequencing of genes whose expression is induced in brain cells, specifically hippocampal neurons, after global ischemia are needed to permit development of techniques by which such genes, their expression products, and antibodies therefor can be employed in studies, diagnoses, and therapies for treatment of disorders such as stroke, epilepsy, neurodegenerative diseases, and cancer.

SUMMARY OF THE INVENTION

Accordingly, it is a primary object of the present invention to provide a gene that has death promoter/suppressor functions.

Another object of the present invention is to provide a gene that has death promoter/suppressor functions in neurons.

Still another object of the present invention is to provide a DNA segment with encodes such a gene.

Another object of the present invention is to identify, clone, and sequence a gene encoding giig15b.

Yet another object of the present invention is to provide a polypeptide corresponding to a giig15b gene.

Another object of the present invention is to provide a polypeptide corresponding to a giig15b gene that can be used to construct drugs that mimic or inhibit its biologic effects.

Yet another object of the present invention is to provide antibodies having binding specificity to the giig15b polypeptide.

Still yet another object of the present invention is to identify a polypeptide sequence that may be used in the treatment of stroke, epilepsy, brain trauma, neurodegenerative diseases, and cancers.

Another object of the present invention is to provide a gene product that can be transfected into neurons or other cells to protect the brain from injury.

Yet another object of the present invention is to provide for recombinant vectors and cells containing the DNA sequence coding for giig15b.

Another object of the present invention is to provide for the production of recombinant giig15b protein.

These and other objects of the present invention are achieved by one or more of the following embodiments.

In one aspect, the invention features a purified isolated DNA molecule comprising a nucleotide sequence that encodes a polypeptide, wherein the polypeptide comprises the amino acid sequence shown in FIG. 2.

In another aspect, the invention features a method of producing recombinant giig15b protein comprising:

a) providing a cell that comprises a purified isolated DNA molecule, wherein the DNA molecule comprises a DNA sequence comprising
 (i) transcriptional and translational control sequences functional in the cell, and (ii) a heterologous coding sequence under the control of the transcriptional and translational sequences, wherein the heterologous coding sequence encodes a polypeptide comprising the amino acid sequence shown in FIG. 2;

b) growing the cell under conditions whereby the polypeptide is expressed, and c) isolating the polypeptide from the cell.

In another aspect, the invention features an antibody selective for giig15b protein.

In yet another aspect, the invention features a method of treating a mammal suffering from a disease state selected from the group consisting of stroke, epilepsy, neurodegenerative disease and cancer, comprising administering to the mammal a therapeutically effective amount of a compound that is based upon or which alters the action of giig15b.

In preferred embodiments, the invention features a DNA molecule with the cDNA sequence shown in FIG. 2.

Other features and advantages of the invention will be apparent from the following description of the preferred embodiment, and from the claims.

BRIEF DESCRIPTION OF THE DRAWINGS

FIG. 2 shows the nucleotide sequence (SEQ ID NO: 1) of the cDNA which encodes giig15b and the deduced amino acid sequence (SEQ ID NO: 2). The homeodomain is underlined.

FIG. 3 shows the alignment of amino acid sequences of the deduced amino acid sequence of giig15b (amino acids 10–73 of SEQ ID NO: 2) with homeodomains from various homeodomain-containing genes (GenBank accession numbers (http://www.ncbi.nim.nih.gov) in parenthesis): Mus musculus oculorhombin (M77842) (SEQ ID NO: 3); chicken transcription factor Pax-6 (S69508) (SEQ ID NO: 4); Brachydanio rerio goosecoid homeodomain protein (L03394) (SEQ ID NO: 5); MUSHOM homeobox protein, MUS musculus (M85271) (SEQ ID NO: 5); oryza sativa (D40856) (SEQ ID NO: 6); xenopus goosecoid homeobox protein (M81481) (SEQ ID NO: 6); Drosphilia melanogaster prd-type homeobox (L08401) (SEQ ID NO: 7); Caenorhabditis elegans mab-18 (U28145) (SEQ ID NO: 8); and Caenorhabditis elegans UNC-30 homeodomain protein (L37867) (SEQ ID NO: 9). Bold boxes indicate identities of amino acids among genes.

In FIG. 4A the giig15b recombinant protein forms a protein/DNA complex with only the $^{32}$P-ATP-labeled homeobox double stranded DNA probe. In FIG. 4B a dose-response relationship between the amount of giig15b protein used and the protein/homeobox DNA binding activity is shown. The same amounts of homeobox DNA probe (30 pg) are used in all reactions. An increase in the amount of giig15b used in reactions results in increased protein/DNA complex production.

DETAILED DESCRIPTION OF THE INVENTION

I. DEFINITIONS

As used herein, the term giig15b refers to a gene induced in rat hippocampal neurons following global ischemia in which the cDNA has an open reading frame of 918 base pairs and which encodes a protein giig15b with a predicted molecular weight of 7.1 kD. The cDNA (SEQ ID NO: 1) and deduced amino acid (SEQ ID NO: 2) sequences are shown in FIG. 2. The homeodomain of this gene is conserved among all species. Its cDNA and antibodies may be used to identify the human counterpart of this gene.

"Global ischemia" means a state in an animal where there is decreased blood flow through the brain.

"Homeodomain" means the highly conserved amino acid sequence within the homeotic proteins that binds to DNA. The "homeodomain consensus binding site" is the DNA sequence to to which the homeotic protein binds.

"Homeobox" and "homeotic" refer to the family of proteins which contain a homeodomain.

"Death regulatory genes" and "death regulatory proteins" refer to genes and proteins that control cell death.

The term "isolated" is used herein to mean set apart from its natural enviornment, e.g., the DNA molecules are separated from the parent chromosome from which they were originally obtained. Thus, "isolated" as used herein includes the presence of DNA molecules in a foreign host or foreign plasmid.

An "ischemia subtraction library" is a set of cDNA clones that is obtained from an enriched proportion of mRNA ischemic brain compared to nonischemic brain.

II. METHODS

Figure 1:
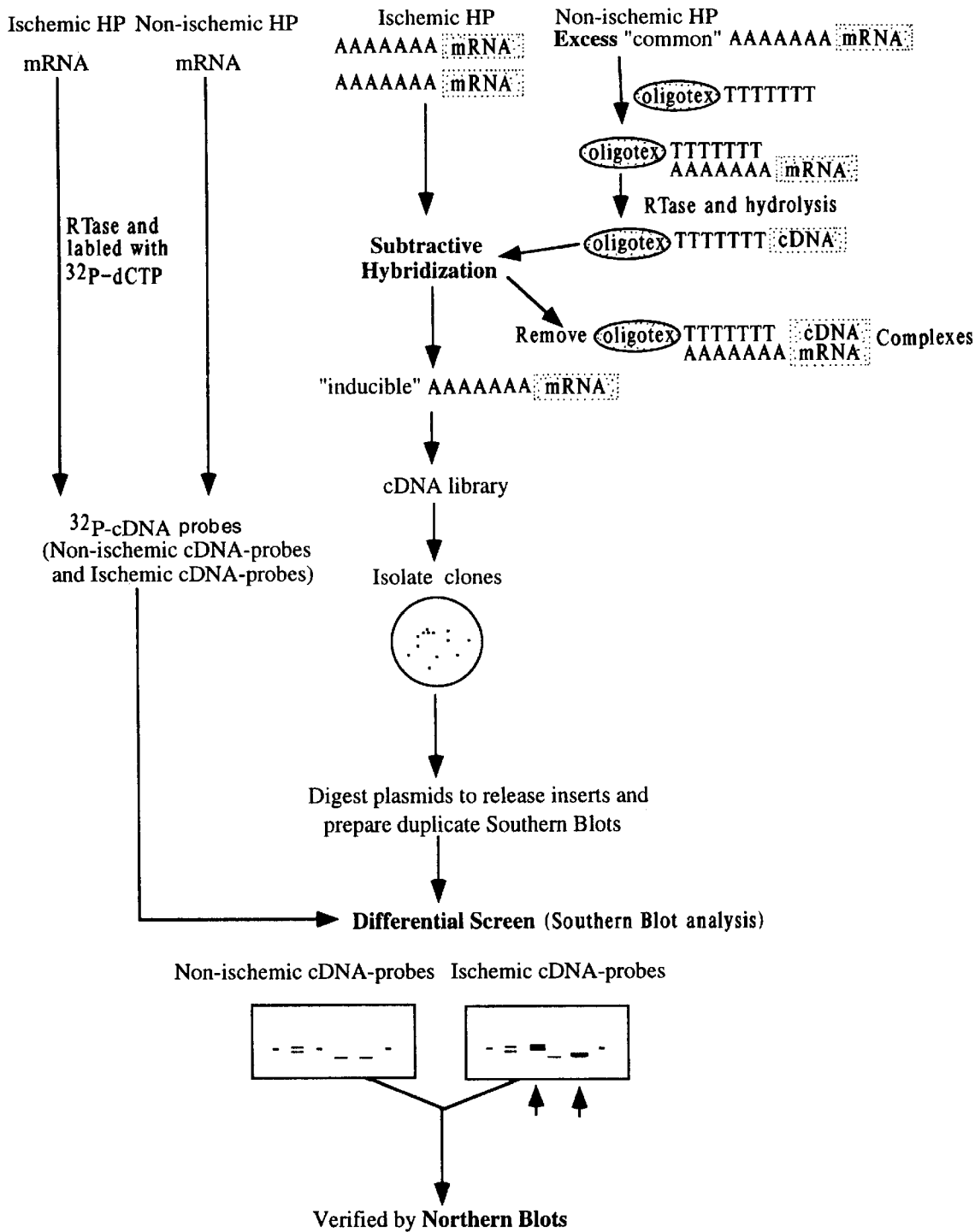
FIG. 1 is a flow chart showing the scheme for constructing a subtractive cDNA library and the differential screening strategy used to obtain the giig15b gene.

According to the present invention, a gene termed giig15b was identified from an ischemia subtraction library of mRNA from rats subjected to global ischemia as shown schematically in FIG. 1. The open reading frame of the resulting cDNA contains 918 base pairs and encodes a protein with a predicted MW of 7.1 kD. The cDNA (SEQ ID NO: 1) and deduced amino acid (SEQ ID NO: 2) sequences are shown in FIG. 2. The cDNA was used to express the protein in an in vitro translation assay. An approximately 7.1 kD protein was produced, suggesting that the deduced protein sequence is accurate. Homology with known proteins was determined with the BLAST searching program at the NCBI (National Center for Biotechnology Information of the National Library of Medicine). The deduced protein sequence of giig15b is highly homologous ($p<10^{-30}$) to many members of the homeobox family of transcription factors. FIG. 3 illustrates the comparisons of giig15b homeodomain amino acid sequence with that of a variety of homeodomain-containing genes.

A giig15b recombinant protein was produced and a gel shift assay was performed which shows that the purified protein binds with the double stranded DNA sequence 5'-CTGGGAATCAATTAAATAATGGCTCG -3' (SEQ ID NO: 11), which contains the homeobox consensus sequence 5'-TCAATTAAAT-3' (SEQ ID NO: 10). The recombinant giig15b protein does not bind with the GRE, CREB, OCT-1 or NFKB1 binding sequences (FIG. 4A) A dose response relationship exists between the amount of giig15b protein and the gel shift assay results (FIG. 4B). These results were further confirmed by fingerprint analysis. A double stranded DNA was synthesized which contains the consensus sequence. Fingerprint analysis confirms that the giig15b protein binds to the homeobox consensus sequence (FIG. 5). These results confirm that giig15b is a novel homeobox protein and suggests that it is a transcription factor.

Figure 6:
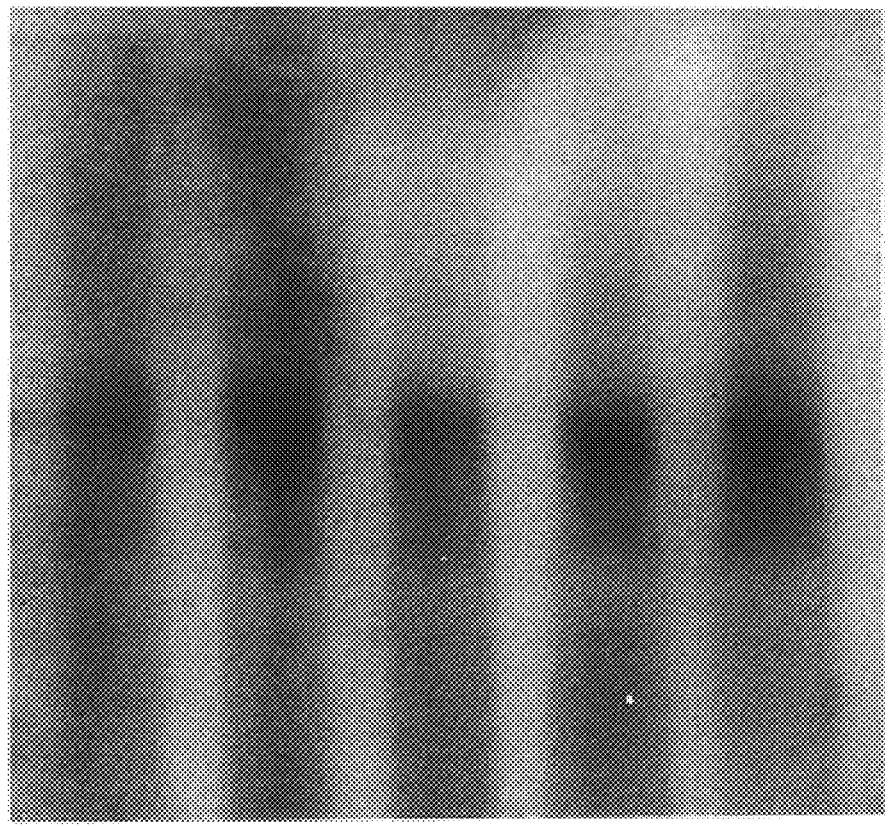
FIG. 6 shows a photograph of a Northern blot of the expression of rat giig15b mRNA. Hippocampal total RNA was extracted from normal non-ischemic brains (Control), brains subjected to 15 minutes of global ischemia followed by 8 hours or 24 hours of reperfusion (Global Ischemia 8h or 24h, respectively), or brains from kainate-induced epilepsy (KA Model 8h and 24h, respectively). Equal amounts of the RNA samples (20 $\mu$g/sample) were separated in a formaldehyde-agarose gel, transferred to a nylon filter, and hybridized with a $^{32}$P-labeled giig15b cDNA probe. One mRNA transcript at approximately 1.0 Kb (indicated) was detected in ischemic and kainate samples.

The expression of giig15b mRNA in the rat brain using Northern blot analysis and in situ hybridization was also explored. In Northern blotting, it was found that giig15b mRNA was increased in brains following ischemia and in brains following kainate-induced epileptic seizures (FIG. 6). In situ hybridization showed that giig15b mRNA was selectively and persistently overexpressed in the CA1 region 24–72 hours (FIG. 7) after ischemia when neurons are dying in this region. A polyclonal antibody was also produced as described herein which recognizes the recombinant giig15b protein at approximately 14 kD. The recombinant protein contains the native protein and the HisTag lead peptide (6.5 kD). The antibody also detects increased expression of the native giig15b protein (approximately 7.1 kD) in rat brain at 24 hr after ischemia (FIG. 8).

The nucleotide and protein sequences, antibodies and recombinant protein of novel genes involved in regulation of cell death have utility as reagents for scientific research, and may have utility as diagnostic agents. In order to study the expression of giig15b proteins and mRNA in tissues antibodies and cDNA are required. Such reagents have value for scientific research. Such reagents may also be used to clone homologous human genes.

The homeodomain, the active site of the protein that binds to DNA, is highly conserved from yeast to human. Andrews, et al., *Science* 270:251 (1995). Homeodomain ("homeobox") proteins are transcription factors that have been found to be important in cellular differentiation in development. For example, a homeobox protein that is induced during early development of Drosophilia embryos may determine dorsal-ventral cellular differentiation. Doyle et al., *Nature* 323:76 (1986). There are many homeobox proteins that bind to region of DNA that may either promote or suppress gene expression. Han et al., *Cell* 56:573 (1989). Homeobox proteins also have other functions. For example, Lin-39 is a homeobox protein that is expressed in *C. elegans* and appears to induce death of certain mid-body cells. Clark, et al., *Cell* 74:43 (1993). The results of the present invention suggest that giig15b is a novel homeobox protein whose expression is increased in dying neurons after ischemia and thus could be a novel transcription factor induced in neurons that regulate cell death.

The nucleotide and polypeptide sequence of a death regulatory protein such as that provided by the present invention may also be used to develop new therapies for diseases such as stroke, epilepsy and neurodegenerative diseases where there is excessive neuronal death and may also be used for the therapy of cancer where there is a defect in normal cell death employing art-recognized routes of administration and doses. For example, the polypeptide structure of the expressed gene may be used to develop conventional drugs that either bind to the protein and inhibit its function, or mimic the action of the protein. In recent years several important drugs have been developed using this technique of rational drug design. Such drugs include the HIV protease inhibitors and the novel selective cyclooxygenase-2 inhibitor family of non-toxic, nonsteroidal anti-inflammatory drugs. Linnik, M.D., et al., *Stroke* 24:2002 (1993). The gene itself may also be used as a therapeutic agent. Gene therapy techniques include viral vector and liposome mediated transfection to yield transformed host cells by techniques well known in the art. Finally, the nucleotide sequence of the gene may be used to produce antisense treatments that block expression of the target protein The antibodies having binding specificity to the giig15b protein of the present invention may be polyclonal or monoclonal. Polyclonal antibodies to the purified protein can be prepared by conventional means as described herein. Monoclonal antibodies to the purified protein polypeptide can be prepared by conventional means as described in Kohler, et al., *Nature* 256:495 (1975).

The DNA sequence isolated and cloned in the present invention code for giig15b. The most preferred embodiment of the present invention is the DNA sequence (SEQ ID NO: 1) shown in FIG. 2. Of course it will be recognized by those skilled in the art that the DNA sequences may vary due to the degeneracy of the genetic code. All DNA sequences which code for the giig15b protein (SEQ ID NO: 2) shown in FIG. 2 are included in the present invention. Additionally, it will be recognized by those skilled in the art that allelic variations may occur in the DNA sequences which will not significantly change the activity or the amino acid sequence of the polypeptide for which the DNA sequence codes. These allelic variations are also covered by the present invention.

It should also be noted that amino acid sequences may exist or be constructed which are substantially similar to the polypeptide shown in FIG. 2 (SEQ ID NO: 2) and which perform substantially the same death promoter/suppressor functions. It will be recognized by those skilled in the art that amino acid sequence changes can be made that will, for example, increase or decrease the biological activity of the specific polypeptide without changing the nature of its function. DNA sequences coding for these polypeptides are also covered by the present invention.

The isolated DNA molecules of the present invention encoding the giig15b gene can be cloned in any suitable plasmid or vector, and used, for example, to produce large amounts of DNA for use as probes or therapeutic agents.

The following example is provided by way of illustration and is in no way intended to limit the scope of the present invention in any way. All reagents not attributed to a specific source were obtained from Sigma Chemical Co., St. Louis, Mo.

EXAMPLE

Ischemic Model

Global ischemia was induced in isoflurane-anesthetized rats using the method originally described by Pulsinelli, W. A., et al., *Ann. Neurol.* 11:491 (1982). Male Sprague-Dawley rats (300–350 g) (Charles River Labs, Wilmington, Mass.) were induced with 5% insoflurane (Malinkrodt Veterinary, Inc., Mondelein, Ill.) by face mask, intubated endotracheally, and ventilated with 1% insoflurane in a mixture of 25% $O_2$ and 74%. $N_2O$. The left femoral artery was cannulated for blood pressure monitoring and blood gas sampling. Rectal temperature of the animals was continuously monitored and kept at 37–37.5° C. by use of a heating pad and a heating lamp throughout the experiment. Brain temperature was monitored by a 20-Ga thermocouple implanted in the left striatum and maintained at 37.0±0.2° C. by the use of a heating lamp. Animals were placed in a Kopf stereotaxic frame (D. Kopf Instruments, Tujunga, Calif.), with their bilateral vertebral arteries coagulated and transected at the level of the junction of first and second cervical vertebrae. Their bilateral common carotid arteries (CCAs) were then exposed, their bilateral external carotid arteries were ligated to block the potential collateral flow from vertebral artery system, and the anesthesia was then discontinued. Three minutes later, both common carotid arteries were occluded with micro-vascular clips under continuous monitoring of the electroencephalogram (EEG). The EEG became isoelectric within 10 seconds following CCA occlusion. only animals with complete EEG flattening following both carotid artery occlusion were used for further study.

Poly(A) $^+$RNA Prep

Total RNA was prepared from the hippocampi of four rat brains from each group after global ischemic injury or from control rat brains by the guanidinium thiocyanate single-step method of Chomczynski, P., et al., *Anal. Biochem* 162:156 (1987). Poly(A)$^+$RNA was isolated using the Fast Track™ mRNA Isolation Kit (Invitrogen, San Diego, Calif.) according to the instructions of the manufacturer.

Construction of Subtractive cDNA Library (a) Rats were subjected to 20 minutes of global ischemia produced by the four vessel occlusion method (Pulsinelli, W. A., et al., *Ann. Neurol.* 11:491 (1982)) and sacrificed at 2, 4, 8, 16, 24, and 72 hours after ischemia. A 4-fold excess of non-ischemic rat brain mRNA was reverse-transcribed into cDNA. This cDNA was then hybridized with mRNA from ischemic rat brain. Double stranded species common to both ischemic and non-ischemic brain were then removed. The remaining subtractive mRNA was used to construct the subtracted cDNA library.

cDNA synthesis using Oligotex™ (Quigen, Santa Clara, Calif.): Poly(A)$^+$RNA (10 µg) from normal rat brain hippocampi was mixed with an equal volume of 5% (w/v) Oligotex™ and heated at 70° C. for 5 min followed by rapid cooling in ice water. After adding 1 volume of 2× TMK buffer (100 mM Tris-HCl pH 8.0, 200 mM KCl, 20 mM $MgCl_2$), the mixture was incubated at 37° C. for 20 min and centrifuged at 15,000 rpm for 10 min at room temperature. Oligotex™-mRNA complexes were then resuspended in 400 µl of RT-mixture (50 mM Tris-HCl at pH 8.0, 90 mM KCl, 3 mM $MgCl_2$, 2 mM each of dNTP, 300 units RNase inhibitor (Promega, Madison, Wis.) and 1000 units Super-Script RTII (Gibco BRL), incubated for 1.5 hr at 37° C., heated for 3 min at 90° C., and chilled on ice for 1 min. The dissociated RNA from the cDNA-Oligotex™ complexes were removed by centrifugation. The precipitated cDNA-Oligotex™ complexes were washed twice with TE buffer (10 mM Tris-HCl pH 7.5, 1 mM EDTA) and were then ready for subtractive preparation.

(b) Preparation of subtractive mRNA: The cDNA-Oligotex™ complexes were dissolved in 100 µl of TEN buffer (10 mM Tris-HCl pH 7.5, 1 mM EDTA, 500 mM NaCl) containing 100 µg $(dA)_{30}(dG)_{10}$ (10 mg/ml), heated for 5 min at 65° C. and for 10 min at 37° C. The $(dA)_{30}(dG)_{10}$ unannealed to oligo $(dT)_{16-18}$ was collected by centrifugation and kept at 4° C. for reuse. The precipitate (cDNA-Oligotex™ complexes) was dissolved in 100 µl of hybridization mixture (10 mM Tris-HCl, at pH 7.5, 1 mM EDTA, 100 mM NaCl, 0.1% SDS, and 1 µg oligo$(dT)_{12-18}$) containing 2.5 µg mRNA from ischemic rat brain hippocampi. The hybridization mixture was incubated at 55° C. for 20 min and centrifuged at room temperature for 10 min. The supernatant (the first subtractive mRNA) was collected and stored at 4° C. The pellet was dissolved in 400 μl of TE buffer, heated at 94° C. for 3 min, and rapidly cooled. After centrifugation, the precipitate was washed with TE buffer, dissolved in the $(dA)_{30}(dG)_{10}$ supernatant, and incubated at 37° C. for 10 min. The free $(dA)_{30}(dG)_{10}$ was collected by centrifugation. The precipitate was dissolved in the first subtractive mRNA fraction and the second hybridization was performed at 55° C. for 20 min. This subtractive hybridization was repeated a total of 3 times.

(c) Construction of a subtractive cDNA library: An ischemic cDNA library was constructed using a SuperScript™ Plasmid System for cDNA Synthesis and Plasmid Cloning Kit (Gibco BRL, Grand Island, N.Y.) according to the instructions of the manufacturer. Briefly, first-strand cDNA was synthesized using oligo $(dT)_{12}$-Not I primer adapter (Gibco BRL) and SuperScript RTII; second-strand synthesis was catalyzed by E.coli DNA polymerase I in combination with E.coli RNase H (Sigma) and E.coli DNA ligase (Sigma). A Sal I adapter was added to the 5' side. Double stranded DNA was restricted with Not I and Sal I and selected on a cDNA size fraction column to include molecules >500 bp. The cDNA was ligated into plasmid pSPORT 1 (Gibco BRL) and transformed into E.coli DH5a (Gibco BRL) The ischemic library used here has 1015 positive clones from subtractive mRNA.

Differential Screening

Plasmids (pSPORT I) containing insert were chosen, digested with Pst I and Xba I (Stratagene, La Jolla, Calif.) to release the cDNA insert, and run on duplicate agarose gels with each lane containing DNA of an individual clone. Gels were Southern-blotted and differentially screened with $^{32}$P-labeled cDNA probes from ischemic mRNA and normal mRNA separately. The probes were labeled as described previously. Briefly, poly(A)$^+$RNAs subtracted as stated above from ischemic and normal rat brain hippocampi were used as templates for the synthesis of a $^{32}$p-labeled cDNA probe with random primers and SuperScript RTII. After mRNA was hydrolyzed, cDNA probes (>1×10 cpm/μg) were purified using NucTrap Probe Purification Columns (Stratagene). The clones that hybridized solely or more strongly to ischemic brain cDNA probe compared with control brain cDNA probe were isolated and studied further using Northern blot and in situ hybridization.

Northern Blot Analysis mRNA (20 μg) was separated by electrophoresis on a 1.0% agarose-formaldehyde gel and transferred onto a Hybond-N™ membrane (Amersham, Arlington Heights, Ill.), using the capillary method, in 10× SSC (1× SSC is 0.15 M NaCl and 0.015 M sodium citrate). RNA was UV-crosslinked to the filter by a Statalinker device (Stratagene). Prehybridization was performed in a mixture containing 50% formamide, 5× SSPE (1× SSPE is 0.15 M NaCl, 0.01 M $Na_2HPO_4$ and 1 mM EDTA), 1× Denhardt's solution (100× Denhardt's solution is 2% polyvinylpyrrolidone, 2% BSA, and 2% Ficoll 400), 0.1% SDS, 10% dextran sulfate and 100 μg/ml of sonicated salmon testis DNA (Sigma) at 42° C. for 2 hr. Hybridization was carried out for 24 hr at 42° C. in the same buffer with a random-primed $^{32}$P-labeled probe at 2×10$^6$ cpm/ml. The membrane was washed for 15 min at room temperature in 1× SSC/0.1% SDS, and three times for 15 min each at 60° C.

in 0.1× SSC/1% SDS. Autoradiography was performed at −80° C. with an intensifying screen.

cDNA probe labeling with α-$^{32}$P-dCTP

Plasmids isolated from a subtracive cDNA library were transformed into competent cell HB101 (Gibco BRL). Single host bacterial colonies were picked and grown in 5 ml LB broth (Fisher Scientific, Pittsburgh, PA) containing ampicillin (Sigma) at 37° C. overnight. Plasmid minipreparation was performed using a Wizard™ Minipreps kit (Promega) according to the instructions of the manufacturer. Insert from the plasmid was released with the digestion with restriction enzymes and purified using a Gene Clean™ kit (BIO 101, Vista, Calif.). The probe was labeled by the random-primed method. About 25 ng of insert DNA was dissolved in 20 μl of distilled water in a microcentrifuge tube by heating for 5 min in a boiling water bath, then immediate cooling on ice. Two microliters of a mixture containing 0.5 mM each of dATP, dTTP, and dGTP; 15 μl of random primers buffer mixture (Gibco BRL); 50 μCi of α-$^{32}$P-dCTP; and 3 units of large fragment of DNA Polymerase I (Gibco BRL) were added. The reaction mixture (50 μl of the total volume) was incubated at room temperature for 1 hr. The probe was purified using NucTrap™ Probe Purification Columns (Strategene).

Sequence Analysis

The cDNA clones were sequenced on both strands using a Sequenase II kit (United States Biochemical, Cleveland, Ohio) according to the instructions of the manufacturer. Sequence analyses were performed using MacVector™ Software (International Biotechnologies, Inc., New Haven, Conn.)

In Vitro Transcription and Translation

In vitro transcription was performed using a RNA transcription kit (Stratagene) according to the instructions of the manufacturer. Briefly, 1 μg of linearized plasmid DNA was incubated with 10 units of T7 RNA Polymerase in 40 mM Tris-HCl (pH 8.0), 8 mM $MgCl_2$, 2 mM spermidine, 50 mM NaCl, 40 mM DTT and 2 mM dNTP in a total volume of 25 μl (at 37° C. for 1 hour). The DNA was degraded by adding 200 units of RNase-free DNase (Promega). The RNA was extracted with phenol/chloroform and precipitated. In vitro translation experiments were performed at 30° C. for 1 hour in combination with 100 ng of purified RNA, 2 μl of translation reaction mixture (reticulocyte translation kit, Boehringer Mannheim, Indianapolis, Ind.) 10 μl of rabbit reticulocyte lysate, 100 mM potassium acetate and 1 mM magnesium acetate in the presence of $^{35}$S-methionine (>800 Ci/mmol). The protein products were electrophoresed in a 12% SDS-PAGE gel.

In Situ Hybridization a) Oligonucleotide Technique: The method used is a modification of the method of Schalling, M., et al., Acta. Physiol. Scand. 131:631 (1987). The advantage of this method is that fresh-frozen tissue is used without requiring any pretreatment. Twenty micron frozen sections were cut and mounted onto gelatinized (Probe-On™) slides (Fisher Scientific). About 350 μl of hybridization solution was used to cover two sections per slide and a second slide was placed over the first to sandwich the sections. The hybridization solution contained 1×10$^6$ cpm/ml of $^{35}$S-labeled oligodeoxynucleotides in 20 μl of 4M DTT, 25 μl of salmon sperm DNA (10 mg/ml), and 450 µl of the cocktail (50% formamide, 5× SSC, 2× Denhardt's, 0.2 M Na phosphate buffer at pH 7.4, 5% dextran sulfate, and 5% sarcosyl. Controls consisted of nonischemic brain and sections incubated with a sense oligonucleotide. After hybridizing for 18 hr at 42° C., sections were rinsed twice for 5 seconds each in 1× SCC at room temperature, four times for 15 min in 1× SCC at 55° C., and for 60 min in 1× SCC at room temperature. Sections were then dehydrated in graded concentrations of alcohol and air dried. The slides were autoradiographed on Kodak X-ray film for 3 weeks. For cellular localization of signal, slides were dipped in NTB-2 emulsion (Kodak, Rochester, N.Y.), exposed for 5 weeks at 4° C., developed, and counterstained with cresyl violet.

b) cRNA technique: Rat brains were processed for in situ hybridization as described previously (Wilcox, J. N., et al., *J. Clin. Invest.* 82:1134 (1988)). Ischemic rat brains were extracted and quick frozen in 2-methylbutane (−40° C.), embedded in TBS tissue freezing medium (Traigle Biomedical Sciences, Durham, N.C.) and stored at −80° C. until processing. Tissue was cut into 20 µm sections on Probe-On™ slides at −20° C. on a Minotome cryostat (Fisher Scientific). The slides were pretreated with 4% paraformaldehyde (15 min), PBS (3 washes for 5 min each), and 2 washes (5 min each) in 750 µl acetic anhydride in 0.1 M triethanolamine-HCl (pH 7.5) to permit nonspecific sticking of the probe to charged groups. The hybridization probes were specific $^{35}$S-labeled RNA transcripts complementary to the mRNA obtained after in vitro transcription of the cDNA insert from linearized plasmid, using SP6 RNA polymerase (Stratagene) (antisense probes) or T7 RNA polymerase (sense probes). The transcription was performed using a Stratagene transcription kit according to the instructions of the manufacturer. Briefly, the transcription mixture, containing 0.5 mM each of CTP, GTP, and ATP, 12 mM $^{35}$S-UTP (New England Nuclear, Boston Mass.); 40 units of RNase inhibitor (Gibco BRL); 2 mM spermidine; 10 mM DTT; and 10 units of T7- or SP6-RNA polymerase in 1X transcription buffer were incubated for 1 hr at 37° C., followed by DNase digestion of the template (RQI DNase; Promega), phenol/chloroform extraction, and ethanol precipitation. About 360 µl of hybridization solution was used to cover two sections per slide and a second slide was placed over the first to sandwich the sections. The hybridization solution contained 1×10$^7$ cpm/ml of $^{35}$S-labeled RNA probe, 40 µl of 0.1M DTT, 50 µl of salmon sperm DNA (10 mg/ml) and 900 µl of cocktail. Cocktail consisted of 50% formamide, 5× SSC, 2× Denhardt's, 0.2 M Na phosphate concentrated by ammonium sulfate precipitation or by running on a protein A column. After hybridization for 16–18 hr at 55° C., slides were separated in 5× SSC and 10 µm DTT. Slides were washed 30 min at 65° C. in 50% deionized formamide (Gibco BRL), 2× SSC, and 0.1% BME (Sigma), washed 3 times (10 min each) in NTE (0.5 M NaCl, 10 mM Tris- Hcl pH 8.0. 5 mM EDTA), incubated 30 min at 37° C. in RNase A (Sigma) (20 µg/µl) in NTE, rinsed in NTE 15 min at 37° C. The sections were then washed in 50% formamide, 2× SSC and 0.1 BME for 30 min at 65° C. (made fresh), rinsed in 2× SSC for 15 min at 37° C., then rinsed again in 0.1× SSC for 15 min at 37° C. After the washes, sections were dehydrated by immersion in graded alcohols containing 0.3 M NH$_4$ acetate, and air dried and autoradiographed on Kodak X-ray film for 3 weeks. For cellular localization of signal, slides were dipped in NTB-2 emulsion, exposed for 5 weeks at 4° C., developed, and counterstained with cresyl violet.

Western Analysis

Brain tissue, dissected from hippocampus and cortex, was collected from freshly removed brain sections and lysed in 0.1 M NaCl, 0.01 M Tris-HCl (pH 7.6), 1 mM EDTA (pH 8.0), 1 µg/ml of aprotinin and 100 µg/ml of phenylmethylsulfonylfluoride (Sigma) Lysates were cleared by centrifugation at 14,000× g for 30 minutes at 4° C. and boiled at 100° C. in SDS gel loading buffer (100 mM Tris-Cl, 200 mM dithiothreitol, 4% SDS, 0.2% bromophenol blue and 20% glycerol) for 6 minutes, before being run on a 12% SDS-PAGE gel. Western blots were then performed as described by Sambrook, J., et al., *Molecular Cloning, A Laboratory Manual* (2 ed. 1989), Cold Spring Harbor Laboratory Press. The membrane was incubated in the primary antibody (giig15b) in a dilution range of 1:500 at 4° C. overnight. This was followed by three washes in washing buffer (0.1% Tween-20, 0.5% BSA and 1% nonfat dry milk in 1× PBS buffer) (Sigma) and then by incubation in the alkaline phosphatase-conjugated second antibody at room temperature for 60 minutes. The second antibody was a goat anti-rabbit IgG (Vector Laboratories, Burlingame, Calif.). Chemiluminescent substrate (CSPD 25 mM) was applied to the membrane. The blot was wrapped in plastic wrap and exposed to a Kodak X-OMAT film. The film was developed and the optical density of the bands measured by the MCID image analysis system (Imaging Research Corp., St. Katherine's, Ontario). Controls for non-specific binding included incubating in the absence of the primary antibody, and, for polyclonal antibodies, preabsorbtion of the primary antibody with the target protein.

Means for Quantifying Protein and mRNA Expression

Differences in mRNA and protein expression were quantified on Northern blots and Western blots respectively using the following methods. Autoradiogram signals were quantified by a gel densitometric scanning program using the MCID image analysis system. To control for variation in the amount of total RNA in different samples, all blots were rehybridized with an oligonucleotide probe (5'-ACGGTATCTGATCGTCTTCGAACC-3') (SEQ ID NO: 12) corresponding to 18S RNA. All densitometric values for mRNA of interest were normalized to values for 18S RNA obtained on the same lane. Protein loading of Western blots is standardized by A280 nm measurements.

Immunocytochemistry

Anesthetized rats were perfused with 100 cc of 0.9% saline followed by 400 cc of 4% paraformaldehyde in phosphate-buffered saline pH 7.4. Brains were removed and postfixed for at least 4 hours. Fifty-micron-thick sections were cut on a vibratome and placed in PBS containing 2% horse serum (Sigma), 0.2% Triton X-100 (Sigma) and 0.1% bovine serum albumin (BSA) (Fisher Scientific) for 2 hours. For polyclonal antibodies, pre-immunization or normal serum was used instead of BSA to reduce background. The sections were incubated with primary antibody (giig15b) at 4° C. for 24 hours on a shaker. Sections were then washed in PBS twice. The second antibody was a biotinylated goat anti-rabbit IgG absorbed against rat serum (for monoclonal antibodies as primary antibodies) (Vector Laboratories) or a biotinylated goat anti-rabbit IgG (for polyclonal antibodies as primary antibodies). Sections were then processed with a Vector ABC kit (Vector Laboratories). The horseradish peroxidase reaction was completed with diaminobenzimide (0.05% in PBS, Sigma) and 0.03% hydrogen peroxide. Alternate sections were incubated without primary antibody as a control. Preabsorbtion of the primary antibody with the peptide utilized for immunizations was also used as a control for non-specific biding of polyclonal antibodies. Since the affinity (km) of the antibody for the peptide is not known, concentrations of 0.1, 1.0 and 3.0 μg/ml of peptide for preabsorbtion were used. A second control consisted of preimmunization serum at the same dilution as used for the primary antibody. Western blotting was also employed to assess the specificity of antibodies.

Recombinant Protein

The giig15b insert was cloned into expression plasmid ET-30(+) (Novagen, Madison, Wis.) and then the recombinant plasmid was transformed into BL21 cells (Novagen). The identified single colony was inoculated into LB medium containing the appropriate antibiotic with shaking at 37° C. until $OD_{600}$ reached 0.5. IPTG (Sigma) was added from a 100 mM stock to a final concentration of 0.4 mM and incubated for 2.5 hr. The cells were harvested by centrifugation and resuspended in cold 50 mM Tris-HCL pH 8.0 2 mM EDTA. After centrifugation, cell pellets were resuspended in 1/10 volume of 50 mM Tris-HCl pH 8.0, 2 mM EDTA and recombinant protein was purified with the S.Tag purification kit (Novagen).

Gel Shift Assay

The predicted binding oligonucleotide sequences, TCAATTAAAT (SEQ ID NO: 10), for homeobox protein and other binding oligonucleotides such as c-jun, were constructed as targets. The oligonucleotide (strand A) was labeled using T4 Kinase, in a reaction system with a total volume of 50 μl containing 5 ng of oligonucleotide, 50 mM TrisHCl at pH 7.9, 10 mM $MgCl_2$, 5 mM DTT, 0.1 mM spermidine, 0.1 mM EDTA, 20 μCi of γ- $^{32}P$ ATP, and 5 units T4 polymerase kinase which was incubated for 30 minutes at 37° C. The reaction was stopped by adding 1 μl of 0.5M EDTA. Then 1 μl (5 ng) of unlabeled strand B complementary to labeled strand A was added, annealed for 5 minutes at 60° C. and allowed to cool to room temperature. The target oligonucleotides was purified using Push Columns (Stratagene). The reaction system, containing 17 μl of incubation buffer (Stratagene), 4000–5000 cpm of labeled target double-stranded oligonucleotide, and 5 μl of recombinant giig15b protein or water was incubated for 30 minutes at room temperature, loaded onto an SDS-PAGE gel, and exposed to film overnight at −70° C. using an intensifying screen. The sample (recombinant protein+probe) was compared to the following: negative control (probe only), positive control (protein from Hela cell+64mer probe, Stratagene), and negative control (64mer probe only). Once a positive protein sample was identified, a competition assay was performed to confirm the results.

Production of Polyclonal Antibodies

Peptide sequences (15–25 amino acids long) were synthesized according to the criteria that peptides contain hydrophilic amino acids and proline residues and use the carboxyl-terminal and amino-terminal sequences. Harlow, E., et al., *Antibodies: A Laboratory Manual*, Cold Spring Harbor Laboratory, pp.72–76 (1988). After coupling to the carrier protein BSA, the peptides were used as antigens to immunize rabbits and to produce polyclonal antibodies (Biosynthesis Co, Dallas, Tex.).

The polyclonal antibody was purified using imunoaffinity purification. Briefly, sulfhydryl-containing peptide was dissolved in 2–3 ml of sulfolink coupling buffer (Pierce, Rockford, Ill.) and added to a polyacrylaminde desalting column. The column was mixed for 15 minutes, incubated for 30 minutes at room temperature and washed with 6 ml of sulfolink coupling buffer. Cysteine HCl in sulfolink coupling buffer was added to the column and mixed for 15 minutes, then incubated for 30 minutes at room temperature. After washing with Tris-HCl (pH 7.5), the polyclonal antibody was pushed through the column and bound to the antigen. The unbound antibodies were removed by washing with 10 volumes of 10 mM Tris-HCl (pH 7.5) and then with 20 volumes of 500 mM NaCl, and 10 mM Tris-HCl (pH 7.5). The specific antibody was eluted by passing 10 volumes of 100 mM glycine (pH 2.5) through the column. The antibody fractions were combined and dialyzed against PBS with 0.02% sodium azide. If necessary, the antibody was concentrated by ammonium sulfate precipitation or by running on a protein A column.

Footprint Analysis

The target oligonucleotide probe [5'-TCTAGCGC GGGGCGTGTGCAGGCACGGCTCAAT-TAAATTTTTGCACTCGTCCCGGCTCTTTCTA GC-3'] (SEQ ID NO: 13), containing the homeobox binding site (SEQ ID NO: 10) (underlined), was prepared by incubating 10 ng of homeobox double-stranded oligonucleotide fragments (dsDNA) with 1× reverse transcriptase buffer (50 mM Tris-HCl pH 8.3, 75 mM KCl, 3 mM $MgCl_2$), 20 mM of DTT, 40 μM of dATP, 30 μCi of [X-$^{32}P$]dGTP, 30 μCi of $^{32}$PdTTP and 100 U of Moloney murine leukemia virus (MMLV) reverse transcriptase (Stratagene) for 1 hour at 37° C. The probe was purified by precipitation with 950 μl of 100% ethanol followed by extraction with 100 μl of phenolchloroform [1:1(v/v)] and reprecipitation with 300 μl of 100% ethanol. 5 μg of affinity purified recombinant giig15b protein (For negative controls, 5 μl of $H_2O$ was used instead of Giig15b protein) were incubated with 20 μl HotFoot™ incubation buffer (Stratagene), 1 μg of poly(dA-dC)poly (dA-dC) (Sigma) and 2% polyvinyl alcohol for 15 minutes on ice followed by a 2 minute incubation at room temperature. The mixture was incubated in 50 μl of DNase buffer (40 mM Tris-HCl pH 7.5, 6 mM $MgCl_2$ and 2 mM $CaCl_2$) and 0.5U of DNase I for 2 minutes at room temperature. The reaction was stopped by adding 100 μl of DNase stop solution (200 mM NaCl (Sigma), 20 mM EDTA (Sigma), 1% SDS (Bio Rad) and 50 μg/μl yeast tRNA (Gibco BRL). The mixture was extracted with 200 μl of phenol-chloroform [1:1(v/v)] (Gibco BRL) and precipitated with 500 μl of 100% ethanol for 15 minutes on ice followed by briefly rinsing with 70% ice cold ethanol. Gel electrophoresis was then performed by loading 3 μl of the mixture onto a 12% polyacrylamide-7M urea sequencing gel made in TBE buffer (30 mA, 40 V/cm, 1× TBE running buffer). The gel was exposed to film overnight at −70° C.

Viability Assay

3T3 cells (ATCC, Manassas, Va.) were grown at 37° C. in a humidified chamber in Dulbecco's Modified Eagle Medium (DMEM) containing 4,500 mg/L D-glucose, L-glutamine, and pyridoxine hydrochloride (Gibco BRL) supplemented with 10% calf serum and lt penicillin-streptomycin. Plasmid PEGFP-C1 (Clontech, Palo Alto, Calif.) which contains a neomycin/kaneomycin resistance gene and a fluorescent reporter gene was used. The giig15b cDNA was ligated into the vector. The 3T3 cells were transfected with the vector containing giig15b using Tfx-50™ transfection reagent (Promega). Controls used were nontransfected cells (control) and cells transfected with PEGFP-C1 vector not containing the giig15b cDNA (vector). G418 (Clontech) treatment was used to select pure cultures of vector- and giig15b-containing cells.

Cells were counted on a hemocytometer using trypan blue and then plated at $3.0 \times 10^5$ cells per 100 mm tissue culture dish. The cells were given time to attach to the dish. Twelve hours after plating, the serum-supplemented medium was removed and replaced with serum-free medium. The cells were washed 3 times in serum-free medium to ensure complete removal of serum. Cells were then incubated at 37° C. and removed to the same centrifuge tube containing the medium. The cells were then spun down to a pellet at 1600 rpm for 10 minutes at 4° C., the supernatant removed, and the cells were then resuspended in 500 $\mu$l of medium. Three samples were collected and incubated in trypan blue for 10 minutes, then counted on a hemocytometer in three different areas of the same volume. Dead cells were counted as those cells which appeared blue under a phase contrast microscope. The counts were then averaged and the percent viable was taken as the number of live cells compared to the total number of cells counted.

III. RESULTS

FIG. 2 illustrates the nucleotide and polypeptide sequence of giig15b as determined by the above methods. FIG. 3 shows the peptide homology alignment constructed using NCBI blast searching. It is seen that within the highly conserved homeodomain, giig15b is highly homologous with a large number of homeodomain containing proteins. However, outside the conserved region, there is no homology at the nucleotide or peptide level with any other known genes as determined by BLAST and FASTA searches (http://www.ncbi.nih.gov). Thus, giig15b is a novel member of the homeobox gene family.

Figure 4A:
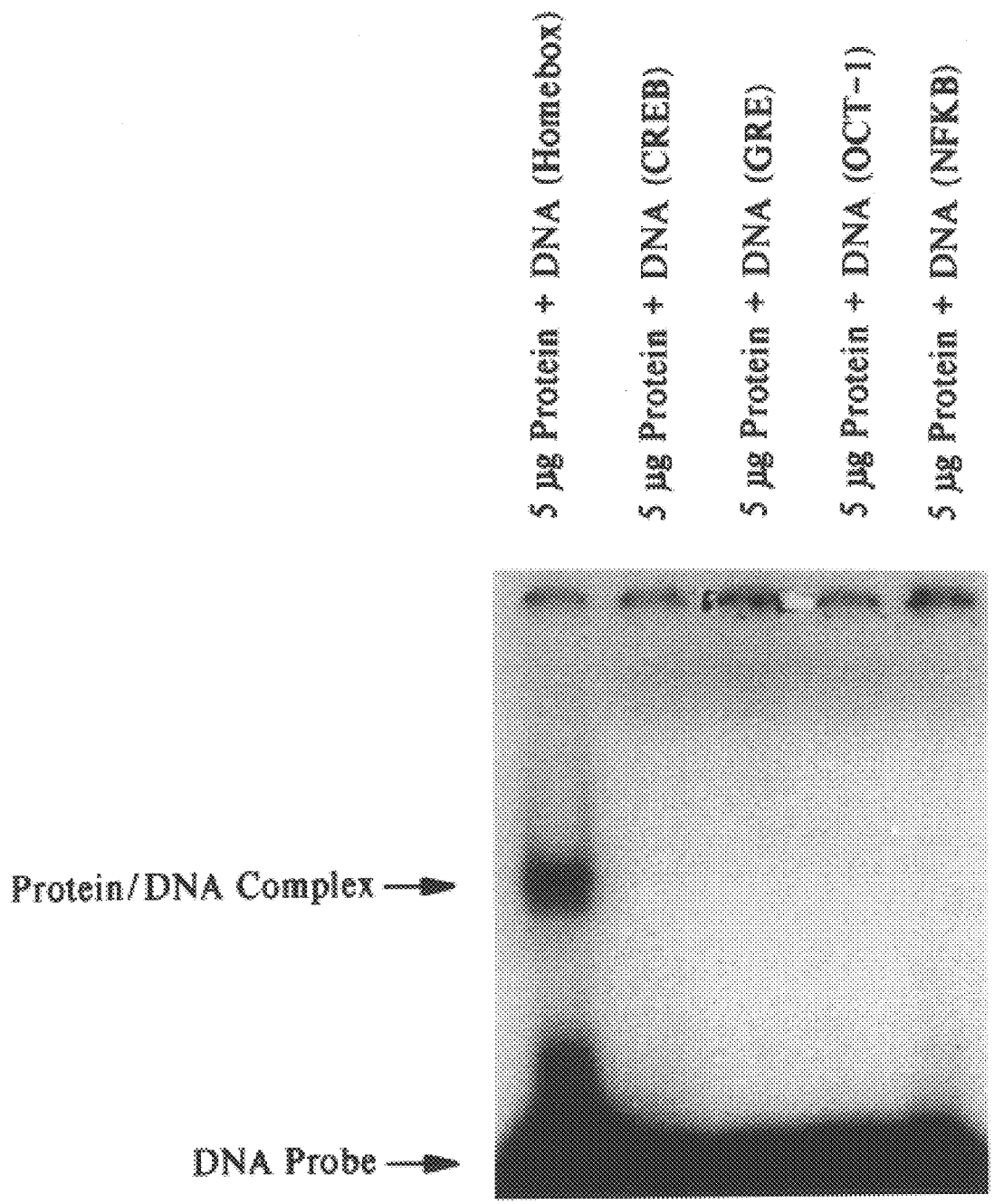
FIGS. 4A and 4B are photographs of gel shift assays performed using the recombinant giig15b protein and the constructed double stranded DNA containing the consensus binding site (5'-TCAATTAAAT-3') (SEQ ID NO: 10) for homeobox protein or containing other common biding sites including CREB, GRE, OCT-1 and NFKB1 (30/pg of each).
Figure 4B:
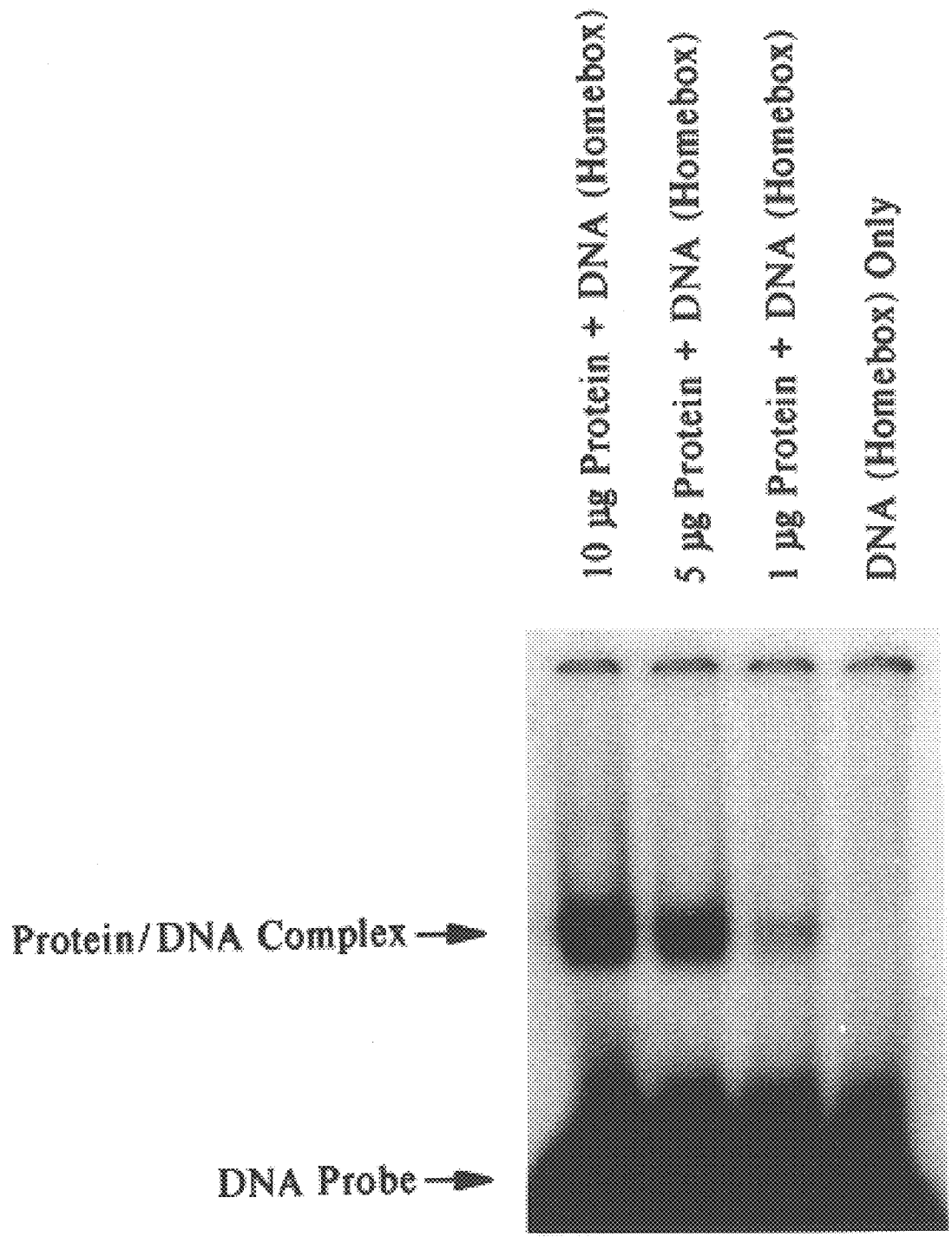
Figure 5:
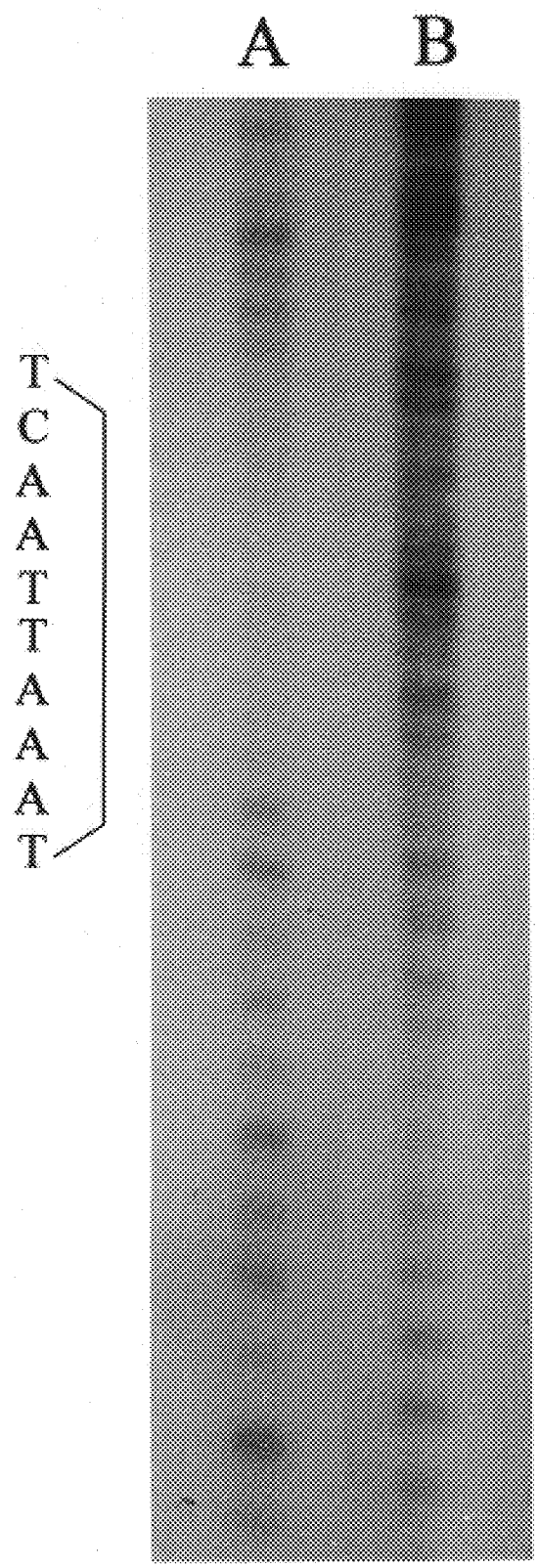
FIG. 5 is a photograph of a $^{32}$P autoradiogram of the giig15b DNA footprint (Lane A) and negative control (Lane B). Both lanes contain 35 pg of the homeobox target oligonucleotide (10,000 cpm). Lane A contains a 25 $\mu$l reaction mix containing giig15b binding protein digested with 0.5 U of DNase/I. The bracket indicates the region of the protected sequence of giig15b protein (5'-TCAATTAAAT-3') (SEQ ID NO: 10) which appears as a "hole" in a ladder of DNA fragments of various lengths. Lane B, the negative control, does not contain giig15b binding protein

FIGS. 4A and 4B illustrate the results of gel shift assays. Recombinant giig15b protein was produced and a double stranded DNA $^{32}$P labeled DNA containing the consensus binding site (5'-TCAATTAAT-3') (SEQ ID NO: 1) for the homeobox protein was synthesized. In addition, DNA oligonucleotides that contain biding sites for common transcription factors, the CREB, GRE OCT-1 and NFKB1 were also labeled. In FIG. 4A these $^{32}$P-labeled oligonucleotides were electrophoresed on a polyacrylamide gel. In one lane, the recombinant giig15 protein (5 $\mu$g) was incubated with the labeled nucleotide containing the homeodomain consensus binding site. The mobility of the $^{32}$P homeodomain consensus binding site oligonucleotide— giig15b protein complex is retarded, thus shifting the band upward compared to oligonucleotides containing binding sites for other transcription factors (lanes 2–5) and the homeodomain consensus site oligonucleotide alone (not shown). In FIG. 4B increasing concentrations of giig15b were mixed with $^{32}$P labeled oligonucleotides containing the homeodomain consensus binding site. A dose response relationship is seen to exist between the concentration of giig15b recombinant protein and the intensity of the shifted band. These results show that the recombinant giig15b binds with double stranded DNA that contains the homeodomain consensus DNA binding site. These results confirm that giig15b is a homeobox gene.

FIG. 5 is a $^{32}$P autoradiograph of the giig15b footprint analysis. In this experiment, a synthetic oligonucleotide containing the homeobox consensus binding site was labeled with $^{32}$P. Oligonucleotide was mixed with recombinant protein and then reacted with transcriptase. The resultant DNA was then digested with DNase and electrophoresed. These results are compared to oligonucleotide that is not mixed with recombinant giig15b protein (lane B). It is seen that the giig15b recombinant protein oligonucleotide mixture contains a hole in the ladder of DNA fragments that corresponds to the portion of the synthetic oligonucleotide that contains the homeodomain consensus binding site. The hole does not appear in lane B, the control, that does not contain the recombinant DNA protein. These results further confirm that the giig15b protein binds to the homeodomain consensus binding site on DNA.

Northern blot analysis (FIG. 6) was performed to study the expression of giig15b messenger RNA in rat brain subjected to ischemia and epilepsy. There is shown increased expression of giig15b messenger RNA at 8 and 24 hours following global ischemia and at 8 and 24 hours after kainate induced epilepsy. Expression of giig15b messenger RNA was studied after global ischemia using in situ hybridization.

Figure 7:
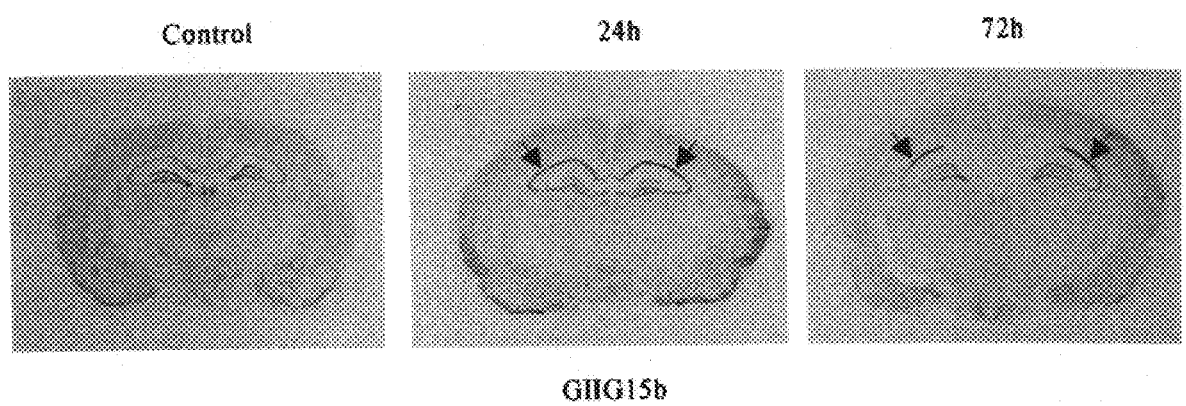
FIG. 7 shows photographs of $^{35}$S in situ hybridization autoradiograms illustrating a control (left) and the induction of giig15b 24h (middle) and 72h (right) after global ischemia. At 24h after global ischemia there is increased expression of mRNA throughout hippocamus and superficial cortex. The region of greatest induction is CA1 (arrows) where there is delayed neuronal necrosis. At 72h after ischemia there is persistent increased expression of mRNA in CA1 (arrows).
Figure 8:
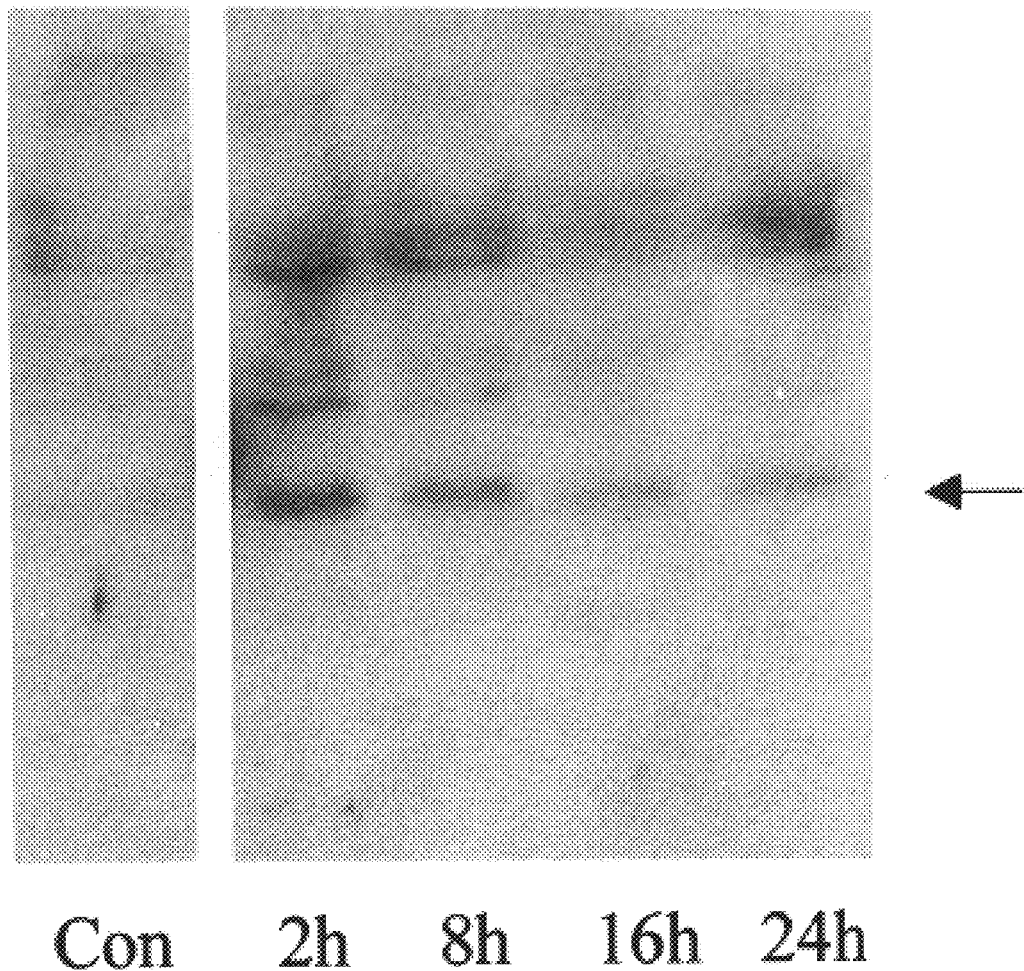
FIG. 8 shows a photograph of a Western blot using affinity purified giig15b antibody to detect a major band at approximately 7.5 kDa in the global ischemia samples. The giig15b protein is detected in the non-ischemia control sample (Con) and at an increased level in hiipocampal samples from rats subjected to 15 min of ischemia and sacrificed 2h, 8h, 16h, and 24h after ischemia (2h, 8h, 16h, 24h, respectively).
Figure 9A:
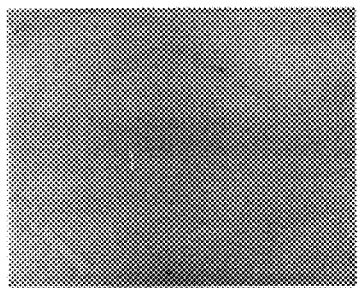
FIGS. 9A–9F are micrographs of giig15b immunocytochemistry in control brains (FIGS. 9A, 9B) and brains at 8h after global ischemia (FIGS. 9C, 9D). giig15b immunoreactivity is increased in large and medium-sized neurons in the CA1 region as compared to normal controls and ischemic brain after the antibody was preabsorbed with the recombinant giig15b peptide (FIGS. 9E, 9F).
Figure 9C:
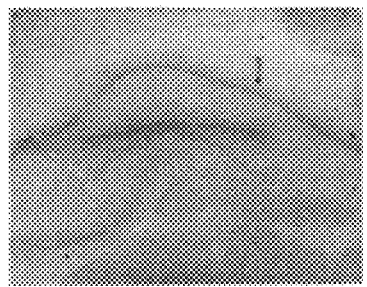
Figure 9E:
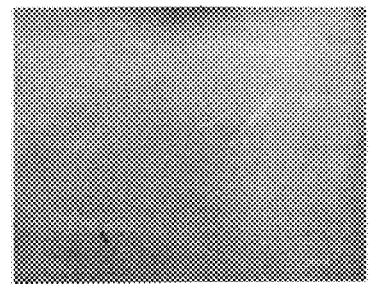
Figure 9B:
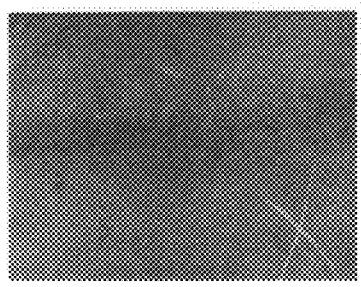
Figure 9D:
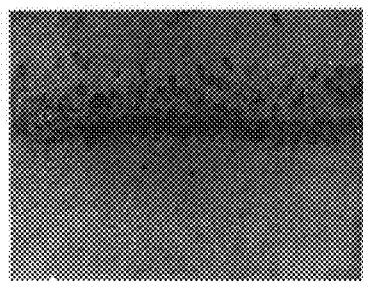
Figure 9F:
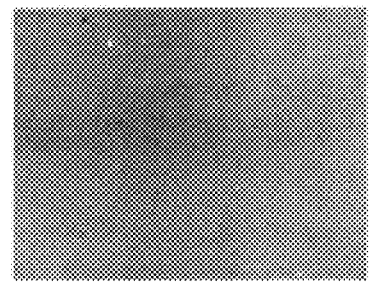

FIG. 7 is autoradiograph of coronal sections of rat brain from a non-ischemic control and brain removed 24 and 72 hours after 15 minutes of global ischemia. At 24 hours after global ischemia, there is shown increased expression of messenger RNA throughout hippocampus. At 72 hours after ischemia, there is a persistent increased expression of messenger RNA in CA1 hippocampus. These results suggest that giig15b messenger RNA is expressed in neurons that are destined to die in this model.

The expression of giig15b protein is also increased after ischemia. FIG. 8 illustrates a Western blot of giig15b protein that is increased after ischemia. Several localizations of giig15b protein were accomplished using immunocytochemistry, as shown in FIGS. 9A–9F. There is increased protein expression of giig15b in the selectively vulnerable CA1 population of neurons. The expression of giig15b protein in these neurons that are undergoing cell death indicate that it may have a death promoter/suppressor role.

Figure 10:
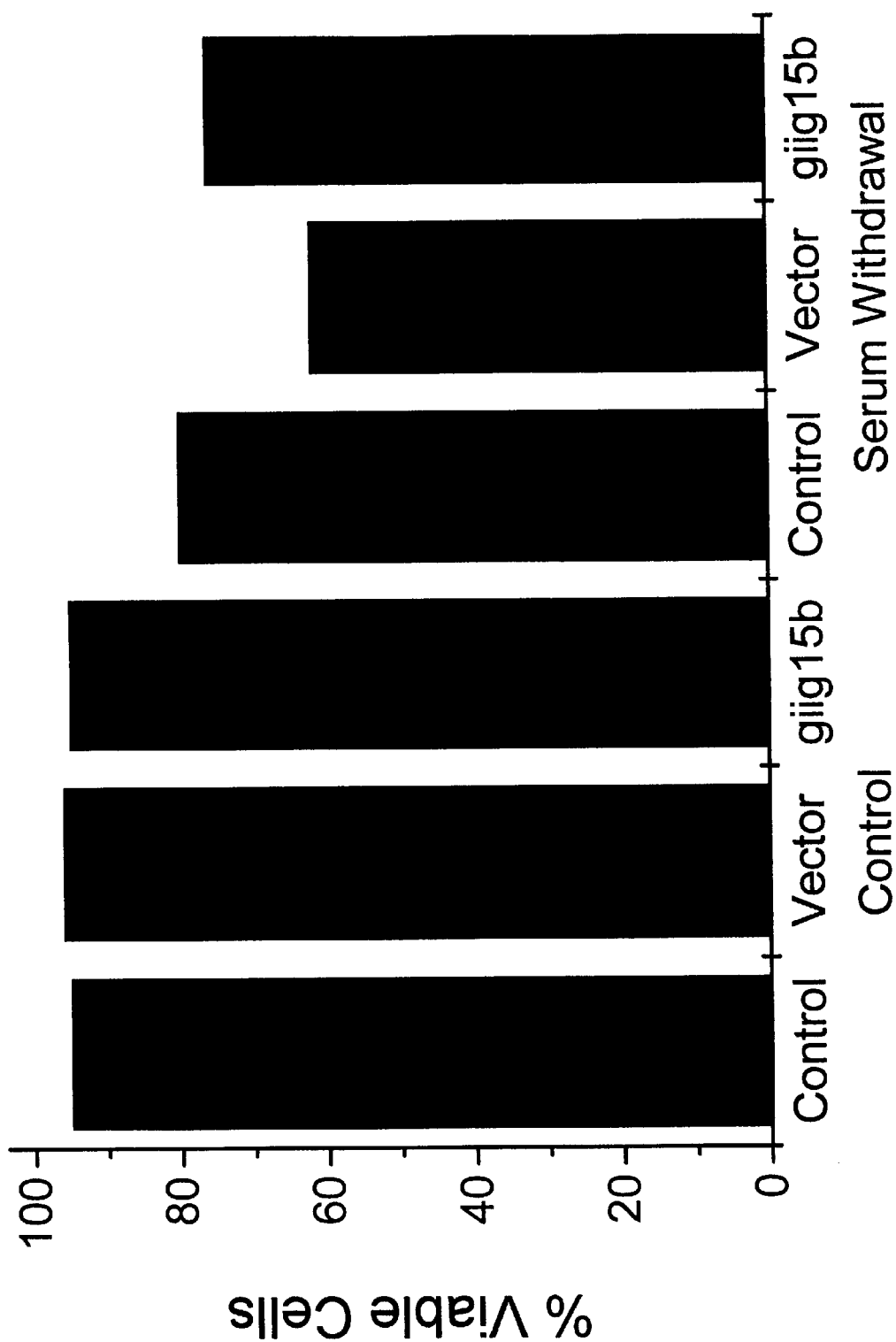
FIG. 10 is a graph illustrating the effect of giig15b transfection upon 3T3 cell survival. giig15b: cells transfected with giig15b-containing vector. Vector: cells transfected with vector without giig15b. Control: nontransfected cells. Serum Withdrawal: percentage of viable cells determined 24 hours after serum withdrawal. Control: percentage of viable cells without serum withdrawal. Each bar indicates the mean of 6–9 determinations.

To test the hypothesis that giig15b has a death promoter/suppressor function, giig15b was transfected in the 3T3 cell line and the effect of transfection upon cell death in vitro determined as shown in FIG. 10. The PEGFP-C1 vector which contains a neomycin/kaneomycin resistance gene and a fluorescent reporter gene was used. The giig15b cDNA was ligated into the vector. 3T3 cells were transfected with the vector containing giig15b (giig15b). Controls consisted of nontransfected cells (Control) and cells transfected with PEGFP-C1 vector not containing the giig15 cDNA (Vector). G418 treatment was used to select pure cultures of vector and giig15b-containing cells. The effect of upon cell death of giig15b expression was determined by inducing apoptosis by withdrawal of serum (serum withdrawal). There was a decreased survival of cells transfected with vector only compared to non-transfected cells after serum withdrawal. This is consistent with a mild toxic effect of transfection. There was no difference seen in survival of giig15b-transfected cells and non-transfected cells, consistent with a protective effect of giig15b transgene expression. Thus giig15b has a death-suppressing effect in 3T3 cells.

The disclosures of all publications referenced above are hereby incorporated in their entirety herein by reference.

Although the invention has been described in detail for the purposes of illustration, it is to be understood that such detail is solely for that purpose and that variations can be made therein by those skilled in the art without departing from the spirit and scope of the invention except as it may be limited by the claims.

We claim:

1. A purified and isolated DNA molecule comprising a nucleotide sequence that encodes a polypeptide, wherein the polypeptide comprises the amino acid sequence (SEQ ID NO: 2) shown in FIG. 2.

2. The DNA molecule of claim 1, wherein the nucleotide sequence is the nucleotide sequence (SEQ ID NO: 1) shown in FIG. 2.

3. The DNA molecule of claim 2, wherein said nucleotide sequence is cDNA (SEQ ID NO: 1).

4. A vector comprising the DNA molecule of claim 1.

5. A recombinant host cell comprising a vector according to claim 4.

6. A method of producing recombinant giig15b protein comprising:

a) growing a cell that contains a DNA molecule, wherein said DNA molecule comprises a DNA sequence comprising (i) transcriptional and translational control sequences functional in said cell, and (ii) a heterologous coding sequence under the control of said transcriptional and translational sequences, wherein the heterologous coding sequence encodes a polypeptide comprising the amino acid sequence shown in FIG. 2 (SEQ ID NO: 2) under conditions whereby said polypeptide is expressed; and b) isolating said polypeptide from said cell.

7. The method of claim 6 wherein said cell is a microorganism.

8. The method of claim 7 wherein said cell is an *E. coli* cell.

9. The method of claim 7 wherein said cell is a yeast cell.

* * * * *

UNITED STATES PATENT AND TRADEMARK OFFICE
CERTIFICATE OF CORRECTION

PATENT NO.   : 5,968,771
DATED        : October 19, 1999
INVENTOR(S)  : Jin et al.

It is certified that error appears in the above-identified patent and that said Letters Patent is hereby corrected as shown below:

Column 1,
Line 2, after title, add
                    -- ACKNOWLEDGEMENT
      The present invention was developed in part with government support under grant number PA-96-071 awarded by the National Institutes of Health. The government has certain rights in this invention. --

Signed and Sealed this

Twelfth Day of October, 2004

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 5,968,771 | Page 1 of 1 |
| DATED | : October 19, 1999 | |
| INVENTOR(S) | : Jin et al. | |

It is certified that error appears in the above-identified patent and that said Letters Patent is hereby corrected as shown below:

<u>Column 1,</u>
Line 2, after title, add
-- <u>ACKNOWLEDGEMENT</u>
   The present invention was developed in part with government support under grant number NS 35936 awarded by the National Institutes of Health. The government has certain rights in this invention. --

This certificate supersedes Certificate of Correction issued October 12, 2004.

Signed and Sealed this

Seventh Day of December, 2004

JON W. DUDAS
*Director of the United States Patent and Trademark Office*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
    (A) LENGTH: 987 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 1:

```
ATCAGCGCTC GCCCAGTCTT CATACGCTCA CGGACC ATG TCG GCG                     45
                                        Met Ser Ala
                                          1

CAG ACT GGC AGC GGC CCC ACG GAG GAC CAG GTG GAG ATC CTG GAG             90
Gln Thr Gly Ser Gly Pro Thr Glu Asp Gln Val Glu Ile Leu Glu
      5              10                  15

TAC AAC TTC AAC AAG GTC AAC AAG CAC CCC GAC CCC ACC ACG CTG            135
Tyr Asn Phe Asn Lys Val Asn Lys His Pro Asp Pro Thr Thr Leu
 20              25                  30

TGC CTC ATC GCA GCC GAG GCG GGC CTC ACG GAG GAG CAG ACG CAG            180
Cys Leu Ile Ala Ala Glu Ala Gly Leu Thr Glu Glu Gln Thr Gln
 35              40                  45

AAA TGG TTT AAG CAG CGC CTG GCG GAG TGG CGG CGG TCA GAA GGC            225
Lys Trp Phe Lys Gln Arg Leu Ala Glu Trp Arg Arg Ser Glu Gly
 50              55                  60

CTG CCT TCG GAA TGC AGA TCG GTC ACG GAC TAGGGAGCCA                     265
Leu Pro Ser Glu Cys Arg Ser Val Thr Asp
 65              70

GGCCCTTGAG CTTGCTCCCG GAACTTCCGT GCCTCAGTTT ACCCAGGCTG                 315

TTTTGATGTT TCAGTGCAGT GTTGAATGTC TCATTGTTTG CTGCCTGCTG                 365

TTTAACACAA TGTGTTTTTT GAATGTATAT AACTAAAGAA ACAAAATAAC                 415

AGGAAGCTAA ATGCAGTTCT GTGTAAAGCG ATGGCTTGGC CGGGAGAGGG                 465

GTGTGGCTTA CGTTTCTCTT TGGATTTTAA TGAAAGATGA TGTGGGAGCA                 515

GTTTTTGTTT GCCCTTGACC GCCACTTTCC AATCCGTATG TACCACCATC                 565

CGTTTCAGAG CATTCCAGAG CTGCCTGGCT TCTGTTGAGA AGTTAAAGGA                 615

ACGGGCAGGC AGGGGAGACA CCTCAGTCCA CCTTCCTGTG CCTCTTTCCT                 665

CGCTTCACTT AACACTCTGG TGGTTGGATG AGAACACGGG TGTATTTGAG                 715

TCATTCAATT TTTATATATT TGAAATATAG ATATATAAAA CAGTTCCTTC                 765

TCTTACAGCT GCGTTACCTT GGAAAACACC CTCGTTTAGC AGCGACAGAT                 815

TCCAAGGGGC AGAAAAGCAG GTAGCTAGGG AAAAAAAGTT ACAGAGTCTA                 865

GAATCTACCT TATTTAAATG AACTTGTTAC ATTTATTTTG CTGAATAACA                 915

TGAACCGCTT TTTTTTGTCT CAAAAATTAT ATTCTAAATA AAAAACTTTG                 965

AGAATCCAAA AAAAAAAAA AA                                                987
```

(2) INFORMATION FOR SEQ ID NO:2:

(i) SEQUENCE CHARACTERISTICS:
    (A) LENGTH: 73 amino acids
    (B) TYPE: amino acid (D) TOPOLOGY:    linear (ii) MOLECULE TYPE:    protein (iii) HYPOTHETICAL:         yes (xi) SEQUENCE DESCRIPTION: SEQ ID NO: 2:

Met Ser Ala Gln Thr Gly Ser Gly Pro Thr Glu Asp Gln Val Glu
1               5                  10                  15

Ile Leu Glu Tyr Asn Phe Asn Lys Val Asn Lys His Pro Asp Pro
                20                  25                  30

Thr Thr Leu Cys Leu Ile Ala Ala Glu Ala Gly Leu Thr Glu Glu
                35                  40                  45

Gln Thr Gln Lys Trp Phe Lys Gln Arg Leu Ala Glu Trp Arg Arg
                50                  55                  60

Ser Glu Gly Leu Pro Ser Glu Cys Arg Ser Val Thr Asp
                65                  70

(2) INFORMATION FOR SEQ ID NO:3:

(i) SEQUENCE CHARACTERISTICS:
        (A) LENGTH:      63 amino acids
        (B) TYPE:        amino acid
        (D) TOPOLOGY:    linear (ii) MOLECULE TYPE:    peptide (iii) HYPOTHETICAL:         yes (xi) SEQUENCE DESCRIPTION: SEQ ID NO: 3:

Thr Gln Glu Gln Ile Glu Ala Leu Glu Lys Glu Phe Glu Arg Thr
1               5                  10                  15

His Tyr Pro Asp Val Phe Ala Arg Glu Arg Leu Ala Ala Lys Ile
                20                  25                  30

Asp Leu Pro Glu Ala Arg Ile Gln Val Trp Phe Ser Asn Arg Arg
                35                  40                  45

Ala Lys Trp Arg Arg Glu Glu Lys Leu Arg Asn Gln Arg Arg Gln
                50                  55                  60

Ala Ser Asn (2) INFORMATION FOR SEQ ID NO:4:

(i) SEQUENCE CHARACTERISTICS:
        (A) LENGTH:      63 amino acids
        (B) TYPE:        amino acid
        (D) TOPOLOGY:    linear (ii) MOLECULE TYPE:    peptide (iii) HYPOTHETICAL:         yes (xi) SEQUENCE DESCRIPTION: SEQ ID NO: 4:

Thr Gln Glu Gln Ile Glu Ala Leu Glu Lys Glu Phe Glu Arg Thr
1               5                  10                  15

Ile Tyr Pro Asp Val Phe Ala Arg Glu Arg Leu Ala Ala Lys Ile
                20                  25                  30

Asp Leu Pro Glu Ala Arg Ile Gln Val Trp Phe Ser Asn Arg Arg
                35                  40                  45

Ala Lys Trp Arg Arg Glu Glu Lys Leu Arg Asn Gln Arg Arg Gln
                50                  55                  60

Ala Ser Asn (2) INFORMATION FOR SEQ ID NO:5:

(i) SEQUENCE CHARACTERISTICS:
        (A) LENGTH: 50 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 5:

```
Thr Asp Glu Gln Leu Glu Ala Leu Glu Asn Leu Phe Gln Glu Thr
 1               5                  10                  15

Lys Tyr Pro Asp Val Gly Thr Arg Glu Gln Leu Ala Arg Lys Val
                20                  25                  30

His Leu Arg Glu Glu Lys Val Glu Val Trp Phe Lys Asn Arg Arg
                35                  40                  45

Ala Lys Trp Arg Arg
                50
```

(2) INFORMATION FOR SEQ ID NO:6:

(i) SEQUENCE CHARACTERISTICS:
        (A) LENGTH: 50 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 6:

```
Thr Asp Glu Gln Leu Glu Ala Leu Glu Asn Leu Phe Gln Glu Thr
 1               5                  10                  15

Lys Tyr Pro Asp Val Gly Thr Arg Glu Gln Leu Ala Arg Arg Val
                20                  25                  30

His Leu Arg Glu Glu Lys Val Glu Val Trp Phe Lys Asn Arg Arg
                35                  40                  45

Ala Lys Trp Arg Arg
                50
```

(2) INFORMATION FOR SEQ ID NO:7:

(i) SEQUENCE CHARACTERISTICS:
        (A) LENGTH: 57 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 7:

```
Gln Leu Glu Glu Leu Glu Lys Ala Phe Ser Arg Thr His Tyr Pro
 1               5                  10                  15

Asp Val Phe Thr Arg Glu Glu Leu Ala Met Lys Ile Gly Leu Thr
                20                  25                  30

Glu Ala Arg Ile Gln Val Trp Phe Gln Asn Arg Arg Ala Lys Trp
                35                  40                  45

Arg Lys Gln Glu Lys Val Gly Pro Gln Ser His Pro
                50                  55
```

(2) INFORMATION FOR SEQ ID NO:8:

(i) SEQUENCE CHARACTERISTICS:
        (A) LENGTH:    59 amino acids
        (B) TYPE:      amino acid
        (D) TOPOLOGY:  linear (ii) MOLECULE TYPE:  peptide (iii) HYPOTHETICAL:       yes (xi) SEQUENCE DESCRIPTION: SEQ ID NO: 8:

Thr Gln Val Gln Ile Glu Ser Leu Glu Lys Glu Phe Glu Arg Thr
1               5                   10                  15

His Tyr Pro Asp Val Phe Ala Arg Glu Arg Leu Ala Gln Lys Ile
            20                  25                  30

Gln Leu Pro Glu Ala Arg Ile Gln Val Trp Phe Ser Asn Arg Arg
            35                  40                  45

Ala Lys Trp Arg Arg Glu Glu Lys Met Arg Asn Lys Arg Ser
            50                  55

(2) INFORMATION FOR SEQ ID NO:9:

(i) SEQUENCE CHARACTERISTICS:
        (A) LENGTH:    52 amino acids
        (B) TYPE:      amino acid
        (D) TOPOLOGY:  linear (ii) MOLECULE TYPE:  peptide (iii) HYPOTHETICAL:       yes (xi) SEQUENCE DESCRIPTION: SEQ ID NO: 9:

Thr Ser His Gln Leu Thr Glu Leu Glu Asn Trp Phe Ser Arg Asn
1               5                   10                  15

Arg Tyr Pro Asp Met Ala Cys Arg Glu Glu Leu Ala Val Trp Ile
            20                  25                  30

Ser Leu Thr Glu Pro Arg Val Arg Val Trp Phe Lys Asn Arg Arg
            35                  40                  45

Ala Lys Trp Arg Lys Arg Glu
            50

(2) INFORMATION FOR SEQ ID NO:10:

(i) SEQUENCE CHARACTERISTICS:
        (A) LENGTH:       10 nucleotides
        (B) TYPE:         nucleic acid
        (C) STRANDEDNESS: single
        (D) TOPOLOGY:     linear (ii) MOLECULE TYPE:        synthetic DNA (xi) SEQUENCE DESCRIPTION:  SEQ ID NO: 10:
        TCAATTAAAT                                                          10

(2) INFORMATION FOR SEQ ID NO:11:

(i) SEQUENCE CHARACTERISTICS:
        (A) LENGTH:       26 nucleotides
        (B) TYPE:         nucleic acid
        (C) STRANDEDNESS: single
        (D) TOPOLOGY:     linear (ii) MOLECULE TYPE:        synthetic DNA (xi) SEQUENCE DESCRIPTION:  SEQ ID NO: 11:

CTGGGAATCA ATTAAATAAT GGCTCG                                               26

(2) INFORMATION FOR SEQ ID NO:12:

```
       (i) SEQUENCE CHARACTERISTICS:
           (A) LENGTH:          24 nucleotides
           (B) TYPE:            nucleic acid
           (C) STRANDEDNESS:    single
           (D) TOPOLOGY:        linear (ii) MOLECULE TYPE:       synthetic DNA (xi) SEQUENCE DESCRIPTION: SEQ ID NO: 12:

ACGGTATCTG ATCGTCTTCG AACC                                              24

(2) INFORMATION FOR SEQ ID NO:13:

(i) SEQUENCE CHARACTERISTICS:
           (A) LENGTH:          66 nucleotides
           (B) TYPE:            nucleic acid
           (C) STRANDEDNESS:    single
           (D) TOPOLOGY:        linear (ii) MOLECULE TYPE:       synthetic DNA (xi) SEQUENCE DESCRIPTION: SEQ ID NO: 13:

TCTAGCGCGG GGCGTGTGCA GGCACGGCTC AATTAAATTT TTGCACTCGT CCCGGCTCTT        60

TCTAGC                                                                  66
```